(12) United States Patent
Hoong et al.

(10) Patent No.: US 7,098,351 B2
(45) Date of Patent: Aug. 29, 2006

(54) PROCESS FOR THE PRODUCTION OF FATTY ACID AMIDES

(75) Inventors: Seng Soi Hoong, Selangor (MY); Salmiah Ahmad, Selangor (MY); Hazimah Abu Hassan, Selangor (MY)

(73) Assignee: Malaysian Palm Oil Board, (MY)

( * ) Notice: Subject to any disclaimer, the term of this patent is extended or adjusted under 35 U.S.C. 154(b) by 0 days.

(21) Appl. No.: 10/997,883

(22) Filed: Nov. 29, 2004

(65) Prior Publication Data

US 2005/0283011 A1     Dec. 22, 2005

(30) Foreign Application Priority Data

Jun. 17, 2004   (MY) .............................. PI 20042370

(51) Int. Cl.
*C07C 51/50*    (2006.01)

(52) U.S. Cl. .......................................... 554/69; 554/68

(58) Field of Classification Search .................. 554/68, 554/69

See application file for complete search history.

(56) References Cited

U.S. PATENT DOCUMENTS

| | | |
|---|---|---|
| 2,013,108 A | 9/1935 | Reppe et al. |
| 2,070,991 A | 2/1937 | Hund et al. |
| 3,253,006 A | 5/1966 | Davis et al. |
| 3,816,483 A | 6/1974 | Werdehausen et al. |
| 4,277,410 A | 7/1981 | Li et al. |
| 4,655,972 A | 4/1987 | Eikelboom et al. |

OTHER PUBLICATIONS

Beckwith, "Synthesis of Amides".
National Dairy Products Corporation, "Manufacture of Amide Compounds", GB 939378, (Oct. 16, 1963).
Cravatt, et al., Structure Determination of an Endogenous Sleep-Inducing Lipid, *cis*-9-Octadecenamide (Oleamide): A Synthetic Approach to the Chemical Analysis of Trace Quantities of Natural Product, 1996 American Chemical Society, pp. 580-590, Sep. 21, 1995.
Jasperse, "The Determination of Fatty Amides by High Performance Liquid Chromatography", JAOCS, vol. 65, No. 11, pp. 1804-1807, (Nov. 1988).

*Primary Examiner*—Deborah D. Carr
(74) *Attorney, Agent, or Firm*—Finnegan, Henderson, Farabow, Garrett & Dunner, LLP

(57) ABSTRACT

This invention discloses a rapid method of production for fatty acid amide from fatty acid and urea. One example is the preparation of oleylamide from oleic acid and urea. The yields are high and oleylamide is selectively formed by judicious choice of catalyst. The production of fatty acid amide involves heating fatty acid and urea in a microwave oven with the use of Lewis acid catalyst. The product from the reaction is subjected to solvent extraction with chloroform and then followed by purification with n-hexane, ethanol and acetonitrile via recrystalization method. Such an oleylamide is preferred for application as a mould release agent, slip agent in plastic film production, water repellent and as a raw material for cosmetics production.

19 Claims, No Drawings

PROCESS FOR THE PRODUCTION OF FATTY ACID AMIDES

FIELD OF THE INVENTION

The present invention relates to a process for the production of fatty acid amides. More particularly, the present invention relates to a process for the production of fatty acid amides, particularly oleylamide, which utilises microwave irradiation as the heating element for the reaction between fatty acids and gaseous ammonia liberated by urea in the presence of a Lewis catalyst at atmospheric pressure and high temperature.

BACKGROUND OF THE INVENTION

Numerous methods are known for the production of fatty acid amide by the reaction of corresponding fatty acid, anhydride or lower alkyl esters thereof with ammonia. These reactions can be accomplished with or without catalyst at elevated temperature and at very high pressure as described in U.S. Pat. No. 3,253,006 but the trend has been to use processes which do not require the use of high pressure and still provide high conversion with high selectivity to the desired amide product. Accordingly, catalytic procedures have been developed whereby the reaction of the fatty acids with ammonia can be achieved by substantially reduced pressures and, in some cases, even at atmospheric pressure.

U.S. Pat. No. 2,013,108 describes a process of atmospheric amidation reaction, which involved passing through gaseous ammonia into the fatty acid melts that contained a surface catalyst, which was a solid inorganic substance. The major drawback -for such process is that it typically requires very long reaction time that may be 48 or more hours to achieve acceptable levels of conversion and consequently some of the amide is dehydrated to the corresponding nitrile.

One of the competing reactions in amidation of carboxylic acids to amide is the dehydration of amide to nitrile, and this is promoted by long reaction time, therefore short reaction time is preferred in order to achieve higher yield of amide. Processes requiring shorter reaction time and employing reaction condition, which minimise undesirable by-product formation, have been developed. According to U.S. Pat. No. 3,816,483, the amidation process can be conducted at atmospheric pressure coupled with shorter time of reaction (11 hours); the formation of nitrile by-product is reduced. The catalysts used in this process are from the Group IVb or Vb metal, preferably a compound of titanium, zirconium or tantalum.

Furthermore, in U.S. Pat. No. 4,277,410, the same approach of amidation reaction is used but the catalyst employed is more specifically to alkyltin catalyst in an amount of 0.25% to 4% by weight. Other than that, U.S. Pat. No. 4,655,972 discloses the use of catalytic amount of hydrated oxide, preferably hydrated titanium, zirconium and tin oxide in an amount of 0.05% to 10% by weight. This process requires high. temperature which is in the range of 120° C. to 240° C. and pressure which is in the range of 100 kPa to 1000 kPa to achieve a good yield.

In view of starting materials for the synthesis of fatty acid amide, most commonly used raw material is the fatty acid itself, but British Patent No. GB 939378 discloses the use of long carbon chain fatty esters (C12 to C30) as the feed stock and reacting it with gaseous ammonia under high pressure and temperature. Non patent literature (Cravatt et al) revealed the use of acid halide typically the one with chlorine atom, which is more reactive compare to fatty acid and esters when react with ammonia.

On the other hand, most of the prior art use gaseous ammonia as starting material to react with the fatty moiety to give the desired amide. in Cravatt et al, urea and thiourea (Beckwith) are used instead of ammonia to react with fatty moiety to yield the fatty acid amide. Other than that, the U.S. Pat. No. 2,070,991 discloses the use of liquid ammonia instead of gaseous ammonia for the amidation process.

In general, it can be said that the usual methods have at least one of three serious drawbacks. Either the methods require long reaction time of at least 11 hours as disclosed in U.S. Pat. Nos. 4,277,410 and 4,655,972, or the methods need to be carried out at high temperature and pressure (e.g. 240° C. and 136 atm) as disclosed in U.S. Pat. No. 3,253,006, or the methods require the synthesis of an expensive intermediate compound as found in non patent literature.

Accordingly, it is an object of this invention to provide such a method of synthesis for normal amide of fatty acids. It is a further object of this invention to provide such a method of synthesis that will give high percentage yield of amide with a short reaction time. It is a still further object of this invention to provide such a method of synthesis that does not require the use of expensive intermediate compounds. It is another object of this invention to provide such a method of synthesis that does not require high pressure to give high percentage yield of fatty amide.

SUMMARY OF THE INVENTION

Accordingly, there is provided a process for the production of fatty acid amides, the process comprises the steps of (a) combining an effective amount of fatty acid with an effective amount of a nitrogenous compound and (b) stirring and heating the mixture obtained from step (a) in a microwave oven, equipment or generator at a temperature of between 140° C. to 250° C. and at a predetermined pressure for a period of 10 to 30 minutes in the presence of a catalyst, wherein the amount of the catalyst is between 0.5 to 10 wt %.

The present invention consists of certain novel features and a combination of parts hereinafter fully described and particularly pointed out in the appended claims, it. being understood that various changes in the details may be without departing from the scope of the invention, or sacrificing any of the advantage of the present invention.

DETAILED DESCRIPTION OF THE PREFERRED EMBODIMENTS

The present invention relates to a process for the production of fatty acid amides. More particularly, the present invention relates to a process for the production of fatty acid amides, particularly oleylamide, which utilises microwave irradiation as the heating element for the reaction between fatty acids and gaseous ammonia liberated by urea in the presence of a Lewis catalyst at atmospheric pressure and high temperature. Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

For the present invention, 0.5 to 10 wt percent and, more preferably 0.5 to 1 wt percent Lewis acid catalysts were employed based on fatty acid weight. Preferably the Lewis acid catalysts are tetra-n-butyl titanate, tetra-n-ethyl titanate and butyl tin chloride di-hydroxy.

The said fatty acids are preferably long carbon chain fatty acids having a chain length. of 12 to 22 carbon atoms with C18:1 as the major component. The ammonia gas may come from nitrogenous compounds that can liberate gaseous ammonia upon heating such as urea and thiourea. In particular, the ratio between fatty acid and urea is about 2 to 6 moles of urea per mole of fatty acid. While the process can be conducted at temperature as high as 250° C. and under high pressure, it is more preferably to carry out the process at a temperature between 160° C. to 210° C. and at atmospheric pressure.

The product from the reaction was subjected to solvent extraction with chloroform, after which the extraction solvent was filtered from the un-reacted urea. The solvent was then evaporated using rotary evaporator, yielding the crude fatty amide. The yield of crude fatty acid amide is between 91–94% based on the weight of fatty acid. The crude fatty amide was sent for HPLC analysis and based on HPLC chromatogram; the crude fatty acid amide has a purity of about 74%–76% oleylamide (93–96% conversion of oleic acid to oleylamide).

The crude oleylamide was subjected to purification via recrystalisation method with solvents in the following sequence, n-hexane, ethanol and acetonitrile. The yield of. purified oleylamide is about 54% with 90% purity, as analysed through HPLC.

The improved process of this invention is particularly useful for the amidation of aliphatic monocarboxylic acids having from 12 to 22 carbon atoms. Typical aliphatic acids, which can be utilised in the process, are lauric acid, myristic acid, myristoleic acid, palmitic acid, palmitoliec acid, stearic acid, isostearic acid, oleic acid, linoleic acid, elaidic acid, linolenic acid, eleostearic acid, arachidic acid, behenic acid, erucic acid, lignoceric acid, nervonic acid, ricinoleic acid and the like. The improvement in this process is demonstrated with oleic acid (70% purity) where the preparation of oleylamide is described.

The improvement in the process of this invention results from the use of microwave irradiation as the heating element in this invention. As a result, the reaction time is very short and the yield of desired product is considerably high. The reaction was conducted in a 900 W microwave oven and the reactants were placed in a round bottom flask and charged with catalyst. The microwave oven was programmed to heat up to 195° C. from ambient room temperature within 5 minutes and this temperature was maintained for 25 minutes. During the reaction, the reactants were stirred with the aid from a magnetic stirrer.

Process condition and other operational details can be widely varied. The reaction temperature will generally be about 140° C. to 210° C., however temperature as high as 230° C. can be used. As commonly known to those artisans skilled in the art, if the reaction temperature is too high, undesirable side reaction will occur, and if the temperature is too low, the reaction requires excessive time to achieve good yield. For this invention, it is preferred that the temperature be in the range of 180° C. to 200° C. Employing temperatures in this range, it is possible to achieve good conversion with minimal side product while still obtaining acceptable reaction rates.

The use of microwave irradiation in this invention also permits the use of atmospheric pressure for this invention. It is particularly preferred aspect of the invention that the process of the present invention is conducted at atmospheric pressure and by such operation the use of costly high-pressure equipment is avoided.

In this invention, a nitrogenous compound was used, which upon heating will release gaseous ammonia. In particular, urea was used to generate the gaseous ammonia. The amount of urea used for the process was in ratio with the amount of fatty acid, which is about 2 to 6 moles of urea, was employed per mole of fatty acid. The solid urea was mixed together with the fatty acid in the reaction flask, which was then heated with the microwave irradiation until certain temperature; the urea will be melted and begin to liberate gaseous ammonia subsurface to the fatty acid. While it is not necessary to dry the urea or reactant(s), excessive amounts of water should not generally be present therein.

It has been reported that fatty amide can be produced from the reaction between fatty acid and ammonia without the present of a catalyst but the yield of fatty amide is considerably low. Therefore, in this invention a Lewis acid catalyst was employed to increase the rate of reaction between fatty acid and gaseous ammonia liberated by urea. In the process, about 0.5 to 10 wt percent and, more preferably 0.5 to 1.0 wt percent Lewis acid catalysts were employed based on fatty acid weight. Preferably the Lewis acid catalysts are tetra-n-butyl titanate, tetra-n-ethyl titanate and butyl tin chloride di-hydroxy.

The reaction was conveniently followed by determining the acid value of the reaction mixture at the end of the reaction. It is generally desired that at the end of the reaction, the reaction mixture have an acid value of 15 or below. Using the combination of microwave irradiation and catalyst of this invention, it is possible to readily achieve acid value less than 15 in short reaction time without the formation of excessive amounts of undesirable by-product.

Separation of the reaction product was achieved by initially subjecting the product to solvent extraction with chloroform. At this stage, the fatty acid amide and un-reacted fatty acid will be extracted by the solvent, leaving behind un-reacted urea and its derivatives via filtration method. The solvent was then evaporated by using rotary evaporator, leaving behind the crude fatty acid amide. The yield of crude fatty acid amide is between 91–94% based on the weight of fatty acid. Analysis of crude fatty amide sample was achieved by using High Performance Liquid Chromatography (HPLC) method and based on HPLC chromatogram; the crude fatty acid amide has a purity of about 74%–76% oleylamide, which correspond with the purity of oleic acid (70–80%) in the starting raw material. Therefore, the yield of oleylamide from this process is about 93–96%.

The last stage in this process is the purification of the crude oleylamide. This was done with recrystalisation method by using solvents in the following sequence, n-hexane, ethanol and acetonitrile. The ratio between each solvent and crude oleylamide. was fixed at 1 part crude oleylamide to 10 parts of solvent by weight of the crude product. In the end, the yield of purified oleylamide is about 50–54% with 90–95% purity, analysed through HPLC. The melting point of the oleylamide produced is in the range of 73° C.–75° C., in which, it is very close to the melting point of pure oleylamide, 74° C.–75° C.

Such an oleylamide is preferred for application as a mould release agent, slip agent in plastic film production, water repellent and as a raw material for cosmetics production. Following is a description by way of Examples of the process for the production of fatty acid amides.

EXAMPLE 1

Oleic acid (25 g, 74% purity) was charged into a 250 ml round bottom flask and then solid urea beads (22 g) were charged into the same flask together with tetra-n-butyl titanate (0.25 g). The mixture was stirred for a minute with a magnetic stirrer in the 900 W microwave oven cavity. The heating program raised the temperature from ambient to 190° C. in 5 minutes and the temperature was maintained at 190° C. for an additional 25 minutes. During the heating process, urea will melt at temperature above 135° C. and begin to decompose at 150° C. liberating $NH_3$ and $CO_2$. The acid value of the reaction product was determined to be about 10 and the conversion percentage of oleic acid to reaction product based on acid value is about 95%.

EXAMPLE 2

The cooled reaction product from Example 1 was mixed with chloroform and any un-reacted urea will be filtered out from the reaction pr was later evaporated by using rotary evaporator to give the crude oleylamide. The yield for crude oleylamide is 92% based on the weight of oleic acid used. The crude oleylamide was subjected to HPLC analysis and the chromatogram shows that the crude oleylamide has a purity of 75%. Therefore, the conversion/yield from oleic acid to oleylamide is about 93% as the starting material (oleic acid) has a purity of 74% oleic acid.

EXAMPLE 3

The crude oleylamide from Example 2 was purified by subjecting it to a series of recrystalisation. First, it was dissolved in hot n-hexane (50° C.) and the mixture was left to cool. As the mixture's temperature cooled down, oleylamide recrystalised out from the solvent. The oleylamide was filtered from the mixture with Buchner filter and then left to dry. Secondly, the recrystalised oleylamide was then dissolved in hot ethanol (50° C.) and as the mixture cooled down, impurities in the sample recrystalised from the mixture and were filtered. The filtrate was vacuum dried and then it was dissolved in hot acetonitrile (60° C.) where the purified oleylamide recrystalised from the solvent when cooled to room temperature. The yield of oleylamide from this purification process is about 54% and the purity of oleylamide produced is about 90%, while its melting point is about 75° C.

EXAMPLE 4

The same experiment was repeated by using tetra-n-ethyl titanate as the Lewis acid catalyst, while the other reaction parameters remained the same as Example 1. The yield of crude oleylamide from this trial is about 94% based on the weight of oleic acid and HPLC chromatogram shows that the purity of the crude oleylamide produced is about 76%. Therefore the conversion/yield from oleic acid to oleylamide is about 96% as the starting material (oleic acid) has a purity of 74% oleic acid. The same purification process was adopted and the yield is about 55%. The purity of the oleylamide produced is about 95% with a melting point of 74° C.

EXAMPLE 5

The same experiment was repeated by using butyl tin chloride di-hydroxy as the Lewis acid catalyst, while the other reaction parameters remained the same as Example 1. The yield of crude oleylamide from this trial is about 94% based on the weight of oleic acid and HPLC chromatogram shows that the purity of the crude oleylamide produced is about 74%. Therefore the conversion/yield from oleic acid to oleylamide is about 94% as the starting material .(oleic acid) has a purity of 74% oleic acid. The same purification process was adopted and the yield is about 52%. The purity of the oleylamide produced is about 90% with a melting point of 73° C.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

The invention claimed is:

1. A process for the production of fatty acid amides, the process comprises the steps of:
   (a) combining an effective amount of fatty acid with an effective amount of a nitrogenous compound; and
   (b) stirring and heating the mixture obtained from step (a) in a microwave oven, equipment or generator at a temperature of between 140° C. to 250° C. and at a predetermined pressure for a period of 10 to 30 minutes in the presence of a catalyst, wherein the amount of the catalyst is between 0.5 to 10 wt %.

2. The process as claimed in claim 1, wherein the temperature is between 160° C. to 210° C.

3. The process as claimed in claim 1, wherein the process is conducted at pressure of 1 atmosphere.

4. The process as claimed in claim 1, wherein the period of the process is between 15 to 30 minutes.

5. The process as claimed in claim 1, wherein the amount of catalyst employed is 1 wt %.

6. The process as claimed in claim 1, wherein the amides are linear primary fatty amides.

7. The process as claimed in claim 6, wherein the linear primary fatty acid amide is oleylamide.

8. The process as claimed in claim 7, wherein oleylamide is used as a mould release agent, slip agent in plastic film production, water repellent and as a raw material for cosmetics production.

9. The process as claimed in claim 7, wherein impurities in the oleylamide are removed via solvent extraction and recrystalisation methods.

10. The process as claimed in claim 9, wherein the solvent used for solvent extraction is chloroform.

11. The process as claimed in claim 9, wherein the solvents used for recrystalisation are n-hexane, ethanol acetonitrile.

12. The process as claimed in claim 1, wherein the fatty acid has from 12 to 22 carbon atoms.

13. The process as claimed in claim 12, wherein the fatty acid is from vegetable or animal fats.

14. The process as claimed in claim 1, wherein the nitrogenous compound is urea.

15. The process as claimed in claim 14, wherein the urea is technical grade urea.

16. The process as claimed in claim 1, wherein the process is either batch-wise or continuous.

17. The process as claimed in claim 1, wherein the power of the microwave oven, equipment or generator is 900 W.

18. The process as claimed in claim 1, wherein the catalyst used are tetra-n-butyl titanate, tetra-n-ethyl titanate and butyl tin chloride di-hydroxy.

19. The process as claimed in claim 12, wherein the fatty acid is oleic acid with a purity of 70% to 80%.

* * * * *

UNITED STATES PATENT AND TRADEMARK OFFICE
CERTIFICATE OF CORRECTION

PATENT NO. : 7,098,351 B2
APPLICATION NO. : 10/997883
DATED : August 29, 2006
INVENTOR(S) : Seng Soi Hoong et al.

It is certified that error appears in the above-identified patent and that said Letters Patent is hereby corrected as shown below:

Claim 11, column 6, lines 55-56, change "ethanol acetonitrile." to --ethanol and acetonitrile.--.

Signed and Sealed this

Twenty-eighth Day of November, 2006

JON W. DUDAS
*Director of the United States Patent and Trademark Office*